(12) United States Patent
Strickler et al.

(10) Patent No.: US 7,771,740 B2
(45) Date of Patent: Aug. 10, 2010

(54) MEDICAL DEVICES CONTAINING COPOLYMERS WITH GRAFT COPOLYMER ENDBLOCKS FOR DRUG DELIVERY

(75) Inventors: Frederick H. Strickler, Natick, MA (US); Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1764 days.

(21) Appl. No.: 10/894,397

(22) Filed: Jul. 19, 2004

(65) Prior Publication Data

US 2006/0013854 A1    Jan. 19, 2006

(51) Int. Cl.
*A61F 2/00* (2006.01)
*A61F 2/06* (2006.01)
*A61K 9/22* (2006.01)

(52) U.S. Cl. .................. 424/423; 525/224; 525/242; 525/309; 604/96.01; 604/890.1; 604/891.1; 623/1.46

(58) Field of Classification Search ................ 424/423; 604/890.1, 891.1; 623/1.46
See application file for complete search history.

(56) References Cited

U.S. PATENT DOCUMENTS

| | | | | |
|---|---|---|---|---|
| 4,085,168 | A | * | 4/1978 | Milkovich et al. ............ 525/59 |
| 4,812,364 | A | * | 3/1989 | Alberts et al. ................ 428/447 |
| 5,378,760 | A | | 1/1995 | Modic et al. ................... 525/71 |
| 5,738,902 | A | | 4/1998 | Forrestal et al. ............ 427/2.12 |
| 5,814,329 | A | | 9/1998 | Shah ........................... 424/433 |
| 5,919,870 | A | | 7/1999 | Letchford et al. ........ 525/333.2 |
| 6,486,278 | B1 | | 11/2002 | Schiffino et al. ............ 526/160 |
| 6,545,097 | B2 | | 4/2003 | Pinchuk et al. ............. 525/240 |
| 7,364,585 | B2 | * | 4/2008 | Weber ........................ 623/1.15 |
| 2002/0026236 | A1 | * | 2/2002 | Helmus et al. ............. 623/1.42 |
| 2002/0045706 | A1 | * | 4/2002 | Houston et al. ............ 525/100 |
| 2002/0082679 | A1 | * | 6/2002 | Sirhan et al. ................ 623/1.15 |
| 2002/0107330 | A1 | | 8/2002 | Pinchuk et al. ............. 525/242 |
| 2003/0235603 | A1 | | 12/2003 | Schwarz et al. ............. 424/426 |

FOREIGN PATENT DOCUMENTS

EP    0 389 094    9/1990

OTHER PUBLICATIONS

Harris et al. Macromolecules 2002 35:3772-3774.*
Kikuchi et al. Polymer 1995 36:2781-2786.*
Bes et al. European Polymer Journal 2003 39:5-13.*
Sierra et al. Polymer 1997 38:4325-4335.*
Truelsen et al. Macromolecular Rapid Communications 2000 21:98-102.*
IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-).*
Jeffrey Pyun et al., "Synthesis of Nanocomposite Organic/Inorganic Hybrid Materials Using Controlled/"Living" Radical Polymerization," *Chem. Mater.*, vol. 13, 2001, pp. 3436-3448.
Yoav Tsori et al., "Structural Changes in Block Copolymers: Coupling of Electric Field and Mobile Ions," *Physical Review Letters*, vol. 90, No. 14, Apr. 11, 2003, pp. 145504-1-145504-4.
Yoav Tsori et al., "Thin Film Diblock Copolymers in Electric Field: Transition from Perpendicular to Parallel Lamellae," *Macromolecules*, vol. 35, 2002, pp. 5161-5170.
T. Thurn-Albrecht et al., "Overcoming Interfacial Interactions with Electric Fields," *Macromolecules*, vol. 33, 2000, pp. 3250-3253.
Figure: ma991896zf00001. Http://pubs.acs.org/isubscribe/journals/mamobx/33/i09/figures/ma991896zf00001.html. Jul. 18, 2003 download.
Joseph C. Salamone, ed., *Concise Polymeric Materials Encyclopedia*, CRC Press, Boca Raton, FL, 1999, pp. 812-814.
Karl J. Hemmerich, "Radiation Sterilization. Polymer Materials Selection for Radiation Sterilized Products," *Medical Device & Diagnostic Industry*, Feb. 2000. http://www.devicelink.com/mddi/archive/00/02/006.html.
Nicolay V. Tsarevsky et al., "Synthesis of Block Copolymers of Acrylonitrile and n-Butyl Acrylate by Atom Transfer Radical Polymerization. Morphological Studies by Atomic Force Microscopy," *Polymer Preprints*, vol. 43(2), 2002, pp. 207-208.
Yoshiki Nakagawa et al., "Development of Novel Attachable Initiators for Atom Transfer Radical Polymerization. Synthesis of Block and Graft Copolymers from Poly(dimethylsiloxane) Macroinitiators," Polymer, vol. 39, No. 21, 1998, pp. 5163-5170.
Linda S. Flosenzier et al., "The Effects of Blending Small Amounts of Homopolystyrene on the Mechanical Properties of a Low Styrene Content Styrene-Butadiene-Styrene Block Copolymer," *Polymer Engineering and Science*, vol. 30, No. 1, 1990, pp. 49-58.

(Continued)

*Primary Examiner*—S. Tran
*Assistant Examiner*—Caralynne Helm
(74) *Attorney, Agent, or Firm*—Mayer & Williams; David B. Bonham; Keum J. Park

(57) ABSTRACT

The present invention provides a medical device comprising a release region and a therapeutic agent disposed within or beneath the release region, and the release region includes a copolymer comprising a low $T_g$ block and at least one graft copolymer endblock having a main chain and a plurality of side chains.

31 Claims, No Drawings

OTHER PUBLICATIONS

Matyjaszewski, Krzysztof. "Well-Defined (Co)Polymers by Atom Transfer Radical Polymerization". Polymer Preprints. vol. 43. No. 2. p. 34-35. 2002.

Lutz, Jean-Francois; Matyjaszewski, Krzysztof. "Synthesis of Graft Terpolymers Poly (Alkyl Methacrylate)-G-Poly (D-Lactic Acid)/Poly (Dimethyl Siloxane) Using the Grafting Through Method in Atom Transfer Radical Polymerization". Polymer Preprints. vol. 43. No. 2. 2002. pp. 231-232.

Tsarevsky, Nicolay V.; Jia, Shijun; Tang, Chuanbing; Kowalewski, Tomasz; Matyjaszewski, Krysztof. "Synthesis of Block Copolymers of Acrylonitrile and N-Butyl Acrylate by Atom Transfer Radical Polymerization, Morphological Studies by Atomic Force Microscopy". Polymer Preprints. vol. 43. No. 2. 2002. pp. 207-208.

Matyjaszewski, Krzysztof; Shipp, Devon A.; McMurtry, Gabriel P.; Gaynor, Scott G.; Pakula, Tadeusz. "Simple and Effective One-Pot Synthesis of (Meth) Acrylic Block Copolymers Through Atom Transfer Radical Polymerization". Journal of Polymer Science: Part A: Polymer Chemistry. vol. 38. 2000. pp. 2023-2031.

Shipp, Devon A.; Wang, Jen-Lung. Matyjaszewski, Krzysztof. "Synthesis of Acrylate and Methacrylate Block Copolymers Using Atom Transfer Radical Polymerization". Macromolecules. vol. 31. 1998. pp. 8005-8008.

David, Ghislain; Robin, Jean-Jacques; Desmazes-Lacroix, Patrick. "Synthesis of Thermoplastic Elastomer Based on Polystyrene Polydimethysiloxane Block Copolymers". Polymer Preprints. vol. 43. No. 2. 2002. pp. 1095-1096.

Matyjaszewski, Krzysztof; Ziegler, Michael J.; Arehart, Stephen V.; Greszta; Pakula, Tadeusz. "Gradient Copolymers by Atom Transfer Radical Copolymerization". J. Phys. Org. Chem. vol. 13. 2000. pp. 775-786.

Miller, Peter J.; Matyjaszewski, Krzysztof. "Atom Transfer Radical Polymerization of (Meth) Acrylates From Poly(Dimethylsiloxane) Macroinitiators". Macromolecules. vol. 32. 1999. 8760-8767.

Pyun, Jeffrey; Matyjaszewski. "Synthesis of Nanocomposite Organic/Inorganic Hybrid Materials Using Controlled/"Living" Radical Polymerization". Chem. Mater. vol. 13. 2001. pp. 3436-3448.

"Morphology of Block Copolymers". Block Copolymers and Thermoplastic Elastomers. pp. 282-287.

* cited by examiner

US 7,771,740 B2

MEDICAL DEVICES CONTAINING COPOLYMERS WITH GRAFT COPOLYMER ENDBLOCKS FOR DRUG DELIVERY

FIELD OF THE INVENTION

The present invention relates generally to medical devices which contain polymer regions for release of therapeutic agents.

BACKGROUND OF THE INVENTION

Numerous polymer-based medical devices have been developed for the delivery of therapeutic agents to the body. In accordance with some typical delivery strategies, a therapeutic agent is provided within a polymeric carrier layer and/or beneath a polymeric barrier layer that is associated with a medical device. Once the medical device is placed at the desired location within a patient, the therapeutic agent is released from the medical device at a rate that is dependent upon the nature of the polymeric carrier and/or barrier layer.

Materials which are suitable for use in making implantable or insertable medical devices typically exhibit one or more of the qualities of exceptional biocompatibility, extrudability, elasticity, moldability, good fiber forming properties, tensile strength, durability, and the like. Moreover, the physical and chemical characteristics of the device materials can play an important role in determining the final release rate of the therapeutic agent. Although controlled release of a therapeutic agent by means of polymeric materials has existed in various forms for many years, there is a continuing need for improved and more precise drug delivery systems, particularly for those materials whose release rate characteristics of an incorporated therapeutic agent may be readily modulated depending on the required need.

Thus, when such biocompatible materials are utilized as drug delivery systems, it is important to select materials that possess good drug release characteristics and also that are robust enough to withstand the rigors of standard medical device manufacturing processing such as sterilization.

As a specific example, block copolymers of polyisobutylene and polystyrene, for example, polystyrene-polyisobutylene-polystyrene triblock copolymers (SIBS copolymers), which are described in U.S. Pat. No. 6,545,097 to Pinchuk et al., which is hereby incorporated by reference in its entirety, have proven valuable as release polymers in implantable or insertable drug-releasing medical devices. As described in Pinchuk et al., the release profile characteristics of therapeutic agents such as paclitaxel from SIBS copolymer systems demonstrate that these copolymers are effective drug delivery systems for providing therapeutic agents to sites in vivo.

These copolymers are particularly useful for medical device applications because of their excellent mechanical characteristics, biostability and biocompatibility, particularly within the vasculature. The SIBS copolymers exhibit high tensile strength, which frequently ranges from 2,000 to 4,000 psi or more, and resist cracking and other forms of degradation under typical in vivo conditions. Biocompatibility, including vascular compatibility, of these materials has been demonstrated by their tendency to provoke minimal adverse tissue reactions (e.g., as measured by reduced macrophage activity). In addition, these polymers are generally hemocompatible as demonstrated by their ability to minimize thrombotic occlusion of small vessels when applied as a coating on coronary stents.

In addition, these polymers possess many interesting physical and chemical properties sought after in medical devices, due to the combination of the polyisobutylene and polystyrene blocks. Polyisobutylene has a low glass transition temperature ($T_g$) and is soft and elastomeric at room (and body) temperature. Polystyrene, on the other hand, has a much higher $T_g$ and is thus hard at these temperatures. Polystyrene is also thermoplastic in nature, opening up a wide range of processing capabilities. Depending upon the relative amounts of polystyrene and polyisobutylene, the resulting copolymer can be formulated to have a range of hardness, for example, from as soft as about Shore 10A to as hard as about Shore 100D.

Despite these desirable qualities, there is a continuing need for improved materials for use as drug delivery systems. For example, SIBS copolymers are synthesized by a living cationic polymerization process, a complex process that requires stringent reaction conditions and low temperatures. Ionic (cationic and anionic) polymerizations typically require reaction conditions free of moisture, oxygen, as well as impurities. To date, only a limited number of monomers, such as isobutylene, have been polymerized by a living cationic polymerization process, thus restricting the ability to vary the chemical composition of polymers and copolymers produced by this process. Further, the experimental rigor generally involved in ionic polymerizations is often too costly for industrial use and free radical routes are preferred. In addition, homopolymers and copolymers containing polyisobutylene such as a SIBS copolymer may be more susceptible to radiation effects and undergo undesirable changes to its mechanical and drug-eluting properties, especially at the radiation levels typically used for medical device sterilization (e.g., about 1.0 to 5.0 Mrad, or even higher).

Hence, it would be advantageous to provide polymers having various properties that are analogous to those of SIBS copolymers (e.g., drug release characteristics, biostability, biocompatibility, etc.), but which also exhibit potentially improved immunity to radiation-based changes in polymer properties and can be synthesized using a wider array of monomer materials. In addition, it would be advantageous to provide blended copolymers containing SIBS with all of its desirable traits, with other polymer materials that provide other important physical or mechanical properties such as radiation-resistance, cross-linking abilities, and drug release characteristics.

SUMMARY OF THE INVENTION

These and other challenges of the prior art are addressed by the present invention which, in one aspect, provides a medical device comprising a release region and a therapeutic agent disposed within or beneath the release region, where the release region includes a copolymer comprising (a) a low $T_g$ block and (b) a graft copolymer endblock having a main chain and a plurality of side chains.

In another aspect, this invention provides a method of modulating the rate of release of a therapeutic agent from a medical device. In this aspect, at least one and preferably a plurality of release regions are provided, and one or more of these release regions is a carrier region containing one or more therapeutic agents, and one or more of the release regions is a non-drug-containing barrier region. Each release region comprises a phase-separated polymer composition comprising a block or graft copolymer. The release rate of the therapeutic agents from the carrier regions is modulated by changing the number, order, thickness, or relative position of the carrier and barrier regions with respect to one another.

In yet another aspect, this invention provides a multi-layer coating for a medical device comprising a plurality of release regions that contain a phase-separated copolymer. The phase-separated copolymer comprises a low $T_g$ polymer midblock and one or more graft copolymer endblocks. Each release region corresponds to a carrier layer comprising one or more therapeutic agents or a non-drug-containing barrier layer, which layers together form a conformal coating on the medical device.

In a further aspect, this invention provides a medical device comprising at least one release region wherein at least one therapeutic agent is present in the release region, and the release region comprises a blend of a first copolymer and a second copolymer. In some embodiments, the first copolymer is a block copolymer consisting of a low $T_g$ midblock and at least one endblock comprising a graft copolymer having a main chain and a plurality of side chains, while the second copolymer comprises a block copolymer having a low $T_g$ midblock and at least one end block.

In another aspect, the present invention provides a medical device comprising a release region wherein a therapeutic agent is present in the release region and the release region comprises a blend of a first copolymer and a second copolymer. In some embodiments, the first copolymer comprises a midblock comprising poly(siloxane) and endblocks comprising a poly(alkylmethacrylate)-graft-polystyrene copolymer and the second copolymer comprises a midblock comprising polyisobutylene and end blocks comprising polystyrene.

In yet another aspect, the present invention provides a method of controlling the release of a therapeutic agent from a medical device comprising providing a release region for the medical device and controlling the release of the therapeutic agent from the release region by changing the hydrophilicity or hydrophobicity of the polymer composition. In some embodiments, the release region comprises at least a portion of the medical device and further comprises at least one therapeutic agent and a polymer composition comprising two or more immiscible polymer phases. In some embodiments, at least one of the immiscible polymer phases is provided by a graft copolymer comprising a main chain and a plurality of side chains.

One advantage of the present invention is that a variety of materials can be provided for use in release regions of implantable or insertable medical devices.

Another advantage of the present invention is that implantable or insertable medical devices can be provided, from which the release of a therapeutic agent can be modulated.

Another advantage of the present invention is that implantable or insertable medical devices can be provided, which are resistant to the damaging effects of radiation sterilization.

These and other embodiments and advantages of the present invention will become immediately apparent to those of ordinary skill in the art upon review of the Detailed Description and claims to follow.

DETAILED DESCRIPTION OF THE INVENTION

A more complete understanding of the present invention is available by reference to the following detailed description of the embodiments. The appearances of the phrase "in one embodiment" in various places in the specification are, obviously, not necessarily all referring to the same embodiment. The detailed description of the embodiments which follows is intended to illustrate but not limit the invention. The scope of the invention is defined by the appended claims.

In one aspect, the invention provides a medical device comprising a release region and a therapeutic agent disposed within or beneath the release region. The release region includes a copolymer comprising (a) one or more low $T_g$ polymer blocks and (b) one or more graft copolymer endblocks, each endblock having a main chain and a plurality of side chains.

A polymer "block", as used herein, refers to a grouping of 10 or more constitutional units, commonly 20 or more, 50 or more, 100 or more, 200 or more, 500 or more, or even 1000 or more units. A "chain" is a linear (unbranched) grouping of 10 or more constitutional units (i.e., a linear block).

A "low $T_g$ polymer block" is a polymer block that displays one or more glass transition temperatures ($T_g$), as measured by any of a number of techniques including differential scanning calorimetry (DSC), dynamic mechanical analysis (DMA), or dielectric analysis (DEA), that is below ambient temperature, more typically below 25° C., 0° C., −25° C., or even −50° C. "Ambient temperature" is typically 25° C.-45° C., more typically body temperature (e.g., 35° C.-40° C.). As a result of their low glass transition temperature, low $T_g$ polymer blocks are typically elastomeric at ambient temperature. Homopolymers of some low $T_g$ polymer blocks, such as linear or branched silicone (e.g. polydimethylsiloxane), are viscous liquids or millable gums at room temperature and become elastomeric upon covalent cross-linking.

Specific examples of low $T_g$ polymer blocks from which the low $T_g$ polymer blocks of the present invention can be selected include homopolymers and copolymer blocks formed from (or having the appearance of being formed from) the following: acrylic monomers, methacrylic monomers, vinyl ether monomers, cyclic ether monomers, ester monomers, unsaturated hydrocarbon monomers, including alkene monomers such as α-olefins and conjugated diene monomers, halogenated alkene monomers, other halogenated unsaturated hydrocarbon monomers, and siloxane monomers. Numerous specific examples are listed below. The $T_g$ values are published values for homopolymers of the listed monomeric unit.

Specific acrylic monomers include: (a) alkyl acrylates such as methyl acrylate ($T_g$ 110° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) halo-alkyl acrylates such as 2,2,2-trifluoroethyl acrylate ($T_g$ −10° C.) and (e) cyano-alkyl acrylates such as 2-cyanoethyl acrylate ($T_g$ 4° C.).

Specific methacrylic monomers include (a) alkyl methacrylates such as butyl methacrylate ($T_g$ 20° C.), hexyl methacrylate ($T_g$ −5° C.), 2-ethylhexyl methacrylate ($T_g$ −110° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.).

Specific vinyl ether monomers include (a) alkyl vinyl ethers such as methyl vinyl ether ($T_g$ −31° C.), ethyl vinyl ether ($T_g$ 43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.).

Specific cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ –22° C.), 1,2-epoxybutane ($T_g$ –70° C.), 1,2-epoxyoctane ($T_g$ –67° C.) and 1,2-epoxydecane ($T_g$ –70° C.).

Specific ester monomers (other than acrylates and methacrylates) include ethylene malonate ($T_g$ –29° C.), vinyl acetate ($T_g$ 30° C.), and vinyl propionate ($T_g$ 10° C.).

Specific alkene monomers include ethylene, propylene ($T_g$ –8 to –13° C.), isobutylene ($T_g$ –73° C.), 1-butene ($T_g$ –24° C.), trans-butadiene ($T_g$ –58° C.), 4-methyl pentene ($T_g$ 29° C.), 1-octene ($T_g$ –63° C.) and other α-olefins, cis-isoprene ($T_g$ –63° C.), and trans-isoprene ($T_g$ –66° C.).

Specific halogenated alkene monomers include vinylidene chloride ($T_g$ –18° C.), vinylidene fluoride ($T_g$ –40° C.), cis-chlorobutadiene ($T_g$ –20° C.), and trans-chlorobutadiene ($T_g$ –40° C.).

Specific siloxane monomers include dimethylsiloxane ($T_g$ –127° C.), diethylsiloxane, methylethylsiloxane, methylphenylsiloxane ($T_g$ –86° C.), and diphenylsiloxane.

In certain preferred embodiments, the low $T_g$ polymer block is a biostable polymer block. A "biostable" polymer block is one that remains associated with the medical device during its period of residence within a patient. Typical examples of biostable low $T_g$ polymer blocks include polyolefin blocks such as polyisobutylene blocks, polysiloxane blocks and polyacrylates.

The low $T_g$ polymer blocks may be provided in a variety of configurations, including linear and branched configurations. Branched configurations include star-shaped configurations (e.g., configurations in which three or more chains emanate from a single branch point), comb configurations (e.g., configurations having a main chain and a plurality of side chains) and dendritic configurations (e.g., arborescent and hyperbranched polymers). The chains or chains forming low $T_g$ polymer blocks may contain, for example, a repeating series of constitutional units of a single type, or a series of constitutional units of two or more types, for instance, arranged in a repeating (e.g., alternating), random, statistical or gradient distribution.

In certain preferred embodiments, the low $T_g$ polymer blocks, which may constitute, for example, the midblock of a triblock copolymer, or the main chain of the graft copolymers of the present invention, comprise elastomeric components which are based upon homopolymers or copolymers of one or more elastomeric materials, such as polyalkylsiloxanes, polyolefins, polyacrylates or other polymers with a glass transition temperature at or below room temperature, such as polymers of various monomers described above. For example, in certain embodiments, the blocks comprise polyolefinic blocks having alternating quaternary and secondary carbons of the general formulation: —(CRR'—CH$_2$)$_n$—, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups. Preferred polyolefinic blocks include blocks of polymerized isobutylene,

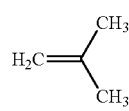

(i.e., polymers where R and R' are the same and are methyl groups).

In other preferred embodiments, polyolefin and polydiene blocks such as functionalized polyolefin and polydiene blocks (which are commercially available with functionalized end groups as poLichelic™ polymers from FMC Lithium, Gastonia, N.C.), as well as variants such as hydrogenated forms of the same, are employed, such as the following.

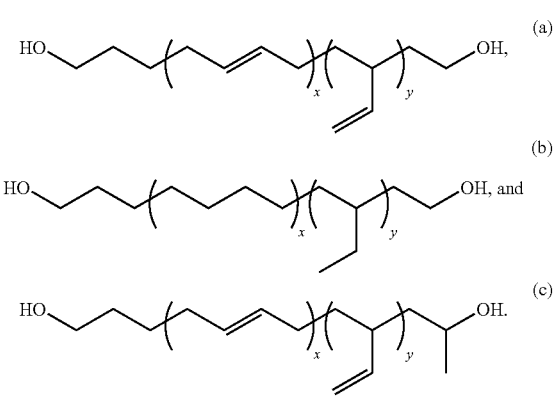

In yet other embodiments, the low $T_g$ polymer block comprises EPDM (ethylene-propylene-diene monomer) copolymer blocks (e.g., Vistalon™ polymers from Exxon-Mobil), which contain units formed from two olefins (ethylene and propylene) and one or more dienes (e.g., vinyl norbornene or ethylidene norbornene), which are illustrated in turn in the following structure:

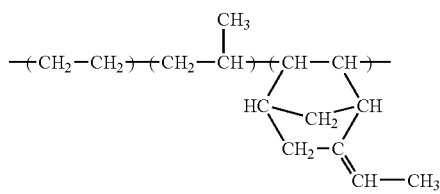

The synthesis of EPDM copolymers is well-known in the art, including preparation via Ziegler-Natta polymerization using homogeneous catalyst compositions based on vanadium, titanium, zirconium, and metallocenes. Details of the preparation of EPDM copolymers are given in U.S. Pat. No. 6,486,278, assigned to ExxonMobil Chemical Patents Inc., the entire contents of which are hereby incorporated by reference.

In some preferred embodiments, the low $T_g$ block comprises a biodisintegrable material (i.e., a material that is subject to dissolution, biodegradation, resorption, etc., during its period of residence within a patient). Preferably, the biodisintegrable material is a polyester block which can be selected, for example, from blocks containing one or more of the following: poly(glycolic acid) blocks, a poly(lactic acid) blocks, a poly(lactic acid-co-glycolic acid) blocks and polycaprolactone blocks.

As noted above, the copolymers of the present invention comprise an endblock (or endblocks) that comprises a main chain and a plurality of side chains. The main and side chains may each independently contain, for example, a repeating series of constitutional units of a single type, or a series of units of two or more types, for instance, arranged in a repeating (e.g., alternating), random, statistical or gradient distribution.

Specific examples of polymer chains from which the main and side chains of the endblock (or endblocks) may independently be selected include homopolymer and copolymer chains formed from (or having the appearance of being formed from) the following: (a) the acrylic monomers, methacrylic monomers, vinyl ether monomers, cyclic ether monomers, ester monomers, alkene monomers, halogenated alkene monomers, and siloxane monomers listed above in connection with the low $T_g$ polymer blocks as well as (b) vinyl aromatic monomers, other vinyl monomers (besides vinyl aromatic monomers), other aromatic monomers (besides vinyl aromatic monomers), other methacrylic monomers (besides the above low $T_g$ methacrylic monomers), other acrylic monomers (besides the above low $T_g$ acrylic monomers), and other alkene monomers (besides the above low $T_g$ alkene monomers).

Vinyl aromatic monomers are those having aromatic and vinyl moieties and include unsubstituted monomers, vinyl-substituted monomers and ring-substituted monomers. Specific vinyl aromatic monomers include the following: (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Specific other vinyl monomers include the following: (a) vinyl alcohol ($T_g$ 85° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.), (d) vinyl halides such as vinyl chloride ($T_g$ 81° C.) and vinyl fluoride ($T_g$ 40° C.); (e) alkyl vinyl ethers such as methyl vinyl ether ($T_g$ −31° C.), propyl vinyl ether ($T_g$ −49° C.), butyl vinyl ether ($T_g$ −55° C.), isobutyl vinyl ether ($T_g$ −19° C.), tert-butyl vinyl ether ($T_g$ 88° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Specific other aromatic monomers, other than vinyl aromatics, include acenaphthalene ($T_g$ 214° C.) and indene ($T_g$ 85° C.).

Specific other methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Specific other acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as isopropyl acrylate ($T_g$ −11° C.), tert-butyl acrylate ($T_g$ 43-107° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.).

Specific other alkene based monomers include the following: ethylene (HDPE) ($T_g$ −125° C.), isotactic propylene ($T_g$ −8° C.), 4-methyl pentene ($T_g$ 29° C.), 1-octadecene ($T_g$ 55° C.), and tetrafluoroethylene ($T_g$ 117° C.).

Typical examples of main chains for the copolymer endblock (or endblocks) include poly(alkyl methacrylates), poly (alkyl acrylates), poly(hydroxyalkyl methacrylates), poly(vinyl esters), polystyrene, polydimethylsiloxane and polyvinylpyridine.

Typical examples of the side chains for the copolymer endblock (or endblocks) include polystyrene, polyethylene oxide, polyvinylpyrrolidone, polymethylmethacrylate and polysiloxanes.

In certain specific embodiments, the main chain or side chains of the endblock (or endblocks) comprise polymer blocks comprising one or more of the biodisintegrable polymer blocks listed herein, for example, one or more polyester blocks selected from a poly(glycolic acid) block, a poly(lactic acid) block, a poly(lactic acid-co-glycolic acid) block and a polycaprolactone block.

In other specific embodiments, the copolymer comprises a polyalkene midblock or a polysiloxane midblock. For example, the copolymer can comprise a polyalkene midblock (such as a polyisobutylene block) or a polysiloxane midblock (such as a polydimethylsiloxane block), and a plurality of endblocks comprising biodisintegrable polyester.

The resulting copolymer, which comprises the low $T_g$ polymer block and the graft copolymer endblock (or endblocks), can be in the form, for example, of a diblock copolymer (e.g., comprising a midblock and a single endblock), a triblock copolymer (e.g., comprising a midblock and a pair of endblocks), a star copolymer (e.g., comprising a midblock and three or more outwardly radiating endblocks), a dendritic copolymer (e.g., comprising a dendritic midblock and a large number of endblocks), or a comb copolymer (e.g., comprising a midblock having a comb configuration and a plurality of endblocks, (which typically also have a comb configuration in the present invention)). Typically, the graft copolymer endblock is also a comb copolymer block comprising, for example, a polyalkene main chain and a plurality of biostable or biodisintegrable polymer side chains.

In certain preferred embodiments, the release regions of the medical devices of the present invention can comprise "hybrid" homopolymers or copolymers (e.g., block, graft or random copolymers) comprising constitutional units having inorganic character, for example, siloxanes, which have both organic and inorganic character. The inherent incompatibility of the constitutional units typically results in phase separation that yields a variety of controlled nanostructures depending on the degree of incompatibility of the constitutional units, the composition, and the degree of polymerization in the final copolymer. For example, graft copolymers can be formulated by chain extending a multifunctional poly(siloxane) macroinitiator with an unsaturated organic monomer, yielding graft copolymers with an main-chain having organic and inorganic character and organic side-chain groups.

For instance, in certain preferred embodiments, the release region of the present invention comprises a hybrid triblock copolymer comprising a low $T_g$ midblock comprising polydimethylsiloxane and two endblocks comprising a main chain and graft side chains, wherein the main chain is formed via an alkyl acrylate-terminated styrene-containing species (e.g., methyl acrylate-terminated styrene-containing macromonomer), such that the graft side chains of the endblocks comprise styrene (e.g., in a random or block copolymer arrangement).

In some preferred embodiments, the graft side chains of the endblock (or endblocks) comprise a hydrophilic polymer such as polyethylene oxide or polyvinylpyrrolidone, or a hydrophobic polymer such as polymethylmethacrylate.

Release regions for use in accordance with the present invention include carrier regions and barrier regions. By "carrier region" is meant a release region which further comprises a therapeutic agent and from which the therapeutic agent is released. For example, in some embodiments, a carrier region is disposed over all or a portion of a medical device, which acts as a substrate. In other embodiments, a carrier region constitutes the entirety of the medical device substrate. By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

Hence, in various embodiments, release regions for use in accordance with the present invention are in the form of a release layer, which covers all or a part of a medical device substrate. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

According to the present invention, the release profile associated with a release region of the medical device can be modified in a number of ways, including, but not limited to, (a) changing the composition of the low $T_g$ polymer block and/or other polymer blocks within the copolymer, thus changing, for example, the biostability, hydrophilicity and/or hydrophobicity of the copolymer, (b) changing the molecular weight of the low $T_g$ polymer and/or other polymer blocks, (c) changing the ratio of the low $T_g$ polymer and other polymer blocks, (d) changing the distribution of the low $T_g$ polymer relative to the other polymer blocks (e.g., midblock vs. endblock), and/or (e) changing the configuration of the copolymer (e.g., a linear low $T_g$ block vs. a branched low $T_g$ block).

The release profile associated with a release region of the medical device can also be modified by changing the number, order, thickness, or position of carrier and barrier regions with respect to one another. For example, the release profile can be modified by varying the thickness of the release region. Moreover, multiple release regions can be employed to modify the release profile. In addition, where a carrier region is employed, a therapeutic-agent concentration gradient can be established within the carrier region to control release of the therapeutic agent.

The release profile associated with the release region can also be modified by blending one or more supplementary polymers with the copolymer within the release region. A variety of polymers are available for use as supplemental polymers in the release regions of the present invention. For example, the supplemental polymer may be a homopolymer or a copolymer (including alternating, random, statistical, gradient and block copolymers), may be cyclic, linear or branched (e.g., the polymers may have star, comb or dendritic architecture), may be natural or synthetic, and may be thermoplastic or thermosetting. Supplemental polymers for the practice of the invention may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

For example, in certain embodiments, the release region comprises a blend of a first copolymer and a second copolymer, at least one of which comprises a graft copolymer block having a main chain and a plurality of side chains and at least one of which comprises a copolymer having a low $T_g$ block. For example, in a preferred embodiment, the blend comprises a first copolymer comprising a triblock graft copolymer consisting of a midblock comprising poly(siloxane) and endblocks comprising a poly(alkylmethacrylate)-graft-polystyrene copolymer and a second copolymer comprising a triblock copolymer having a midblock comprising polyisobutylene and end blocks comprising polystyrene.

In certain embodiments, the medical devices of the present invention can be made by a method that comprises (a) providing a solution comprising (i) a solvent system and (ii) the copolymer; and (b) forming the release region from the solution by removing the solvent system from the solution. The solution can further comprise a therapeutic agent in dissolved or dispersed form, and in some embodiments, the solution is applied over a therapeutic-agent-containing region that comprises said therapeutic agent. As described in detail below, such release regions can be formed by a spraying process or by a variety of other techniques.

Numerous other techniques are available for forming the polymeric release regions of the present invention. For example, where the selected copolymer (and supplemental polymer, if any) has thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the copolymer prior to thermoplastic processing, producing a therapeutic-agent containing carrier region. If not, then a carrier region can nonetheless be formed by subsequent introduction of therapeutic agent, for example, as discussed below.

As indicated above, polymeric release regions can also be formed using solvent-based techniques in which copolymer (and supplemental polymer, if any) is first dissolved or dispersed in a solvent and the resulting mixture is subsequently used to form the polymeric release region.

Where the release region is formed using a solvent-based technique, it is preferably dried after application to remove the solvents. The release region typically further conforms to any underlying surface during the drying process. Where solvent-based techniques are used, the solvent system that is selected will contain one or more solvent species. The solvent system is typically a good solvent for the copolymer and, where included, for the supplemental polymer and the therapeutic agent. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In various embodiments, a mixture containing solvent, copolymer and supplemental polymer, if any, is applied to a substrate to form a release region. For example, the substrate can be all or a portion of an implantable or insertable medical device, such as a stent, to which a release layer is applied. On the other hand, the substrate can also be, for example, a template from which the polymeric release region is removed after solvent elimination. Such template-based techniques are particularly appropriate for forming simple objects such as sheets, tubes, cylinders and so forth, which can be easily removed from a template substrate.

In other techniques, for example, fiber forming techniques, the polymeric release region is formed without the aid of a substrate or template.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to for example, a barrier region), a therapeutic agent can be dissolved or dispersed in the polymer/solvent mixture if desired, and hence co-established with the carrier region. In other embodiments, on the other hand, the therapeutic agent can be dissolved or dispersed within a solvent, and the resulting solution contacted with a polymer region that is previously formed using, for example, one or more of the application techniques described above (e.g., dipping, spraying, etc.).

Barrier layers, on the other hand, are typically formed over a therapeutic-agent-containing region, for example, using solvent-based techniques such as those discussed above in which the copolymer and supplemental polymer, if any, are first dissolved or dispersed in a solvent, and the resulting mixture is subsequently used to form the barrier layer.

In some embodiments, the therapeutic-agent-containing region beneath the barrier region will comprise one or more polymers such as those described elsewhere herein. (The polymeric composition of the barrier region may, or may not be the same as the polymeric composition of the underlying therapeutic-agent-containing region.) As such, the therapeutic-agent-containing region can also be established using techniques (e.g., dipping, spraying, etc.) such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

In some embodiments, the release profile can be modified by providing a separate barrier layer that contains one or more polymers. In other embodiments, the device comprises multiple regions, wherein a plurality of therapeutic-agent-containing regions loaded with varying concentrations of one or more therapeutic agents are interposed beneath barrier layers, such that each therapeutic-agent-containing region is adjacent to one or more barrier layers. Each therapeutic-agent-containing region comprises a copolymer or a blend of polymers comprising hydrophobic and/or hydrophilic polymers.

An overall desired release profile of a therapeutic agent may be achieved by employing a plurality of release regions, which collectively provide an overall desired release profile of a therapeutic agent from the medical device of the present invention. Thus, in one aspect, this invention provides a method of modulating the rate of release of a therapeutic agent from a medical device. In this aspect, a plurality of release regions are provided and one or more of these release regions comprises a carrier region containing one or more therapeutic agents, and one or more of the release regions comprises a non-drug-containing barrier region. Each release region comprises a phase-separated polymer composition comprising a block or graft copolymer.

As suggested above, the release rate of the therapeutic agents from the carrier regions may be modulated by changing one or more of the following: the number, order, thickness, or position of carrier and barrier regions with respect to one another. In some embodiments, the release regions comprise a plurality of layers which form a conformal coating on the medical device, wherein at least one of the layers comprises a barrier region, and at least one of the layers comprises a carrier region. These layers may alternate between carrier and barrier regions, or may comprise two or more layers comprising carrier regions alternating with one or more barrier regions. In some preferred embodiments, a carrier layer is interposed between adjacent barrier layers, and in other preferred embodiments, at least one carrier or barrier region comprises a biodisintegrable polymer. In yet other embodiments, one or more barrier regions may overlap portions of one or more carrier regions, or a single barrier region may be disposed over a plurality of discrete carrier regions. Any such variations in the thickness, number, order or position of the carrier and barrier regions with respect to one another are within the scope of the present invention.

In some embodiments, a plurality of release regions comprising a phase-separated copolymer are provided in the form of layers which together form a multi-layer coating for a medical device, where the phase-separated copolymer comprises a low $T_g$ polymer midblock and one or more graft copolymer endblocks. Each release region is in the form of a carrier layer comprising one or more therapeutic agents or a non-drug-containing barrier layer, which layers together form a conformal coating on the medical device.

In some embodiments, the graft copolymer endblocks of the coating can comprise a cross-linking polymer having two or more immiscible polymer phases. For example, the coating may comprise a first phase comprising a low $T_g$ polymer midblock such as polydimethylsiloxane or polyisobutylene and a second phase comprising a graft copolymer block comprising poly(alkylmethacrylate)-graft-polystyrene copolymer.

As will be described in greater detail to follow, the polymeric materials comprising the release regions of the present invention can be copolymerized to incorporate one or more hydrophilic or hydrophobic monomers, the release regions can include one or more hydrophilic or hydrophobic polymers, or the release regions can comprise a blend of two or more polymers.

In certain embodiments of the present invention, the drug release rate of the therapeutic releasing agent is controlled by changing the hydrophilic/hydrophobic ratio of the block copolymer of the present invention such that the overall hydrophilicity of the copolymer is increased or decreased (or, viewed conversely, the overall hydrophobicity is increased or decreased). As will be appreciated by one of skill in the art, the ratio may be changed in a number of ways.

The hydrophilicity of the block copolymer can be increased by forming copolymers with one or more hydrophilic monomers, such as hydroxyethyl methacrylate, and also including but not limited to those numerous examples of hydrophilic monomers specifically listed above for preparation of low $T_g$ and other polymer blocks and endblocks. In alternative embodiments, the hydrophobicity of the resulting copolymer is increased by forming copolymers with one or more hydrophobic monomers. Any one or more of a number of hydrophobic monomers can be used, including but not limited to methyl methacrylate, as well as those numerous examples of hydrophobic monomers specifically listed above for preparation of low $T_g$ and other polymer blocks and endblocks.

Although one of skill in the art would readily discern whether a monomer is predominantly hydrophilic or hydrophobic, various monomers having hydrophilic or hydrophobic characteristics and which are suitable for use in the present invention and which can be used to modulate the hydrophilic and/or hydrophobic character of the materials of the present invention are exemplified, but not limited, by the following: (1) hydrophobic monomers including the following: vinyl aromatic monomers, including unsubstituted vinyl aromatics, vinyl substituted aromatics, and ring-substituted vinyl aromatics; vinyl esters, vinyl halides, alkyl vinyl ethers, and other vinyl compounds such as vinyl ferrocene; aromatic monomers other than vinyl aromatics, including acenaphthalene and indene; acrylic monomers, including alkyl acrylates, arylalkyl acrylates, alkoxyalkyl acrylates, halo-alkyl acrylates, and cyano-alkyl acrylates; methacrylic monomers, including methacrylic acid esters (methacrylates) and other methacrylic-acid derivatives including methacrylonitrile; acrylic monomers, including acrylic acid esters and other acrylic-acid derivatives including acrylonitrile, alkyl methacrylates and aminoalkyl methacrylates; alkene-based monomers, including ethylene, isotactic propylene, 4-methyl pentene, 1-octadecene, and tetrafluoroethylene and other unsaturated hydrocarbon monomers; cyclic ether monomers; ether monomers other than acrylates and methacrylates; and other monomers including epsilon-caprolactone; and (2) hydrophilic monomers including the following: vinyl amines, alkyl vinyl ethers, 1-vinyl-2-pyrrolidone and other vinyl compounds; methacrylic monomers including methacrylic acid and methacrylic acid salts; acrylic monomers such as acrylic acid, its anhydride and salt forms, and acrylic acid amides; alkyl vinyl ether monomers such as methyl vinyl ether; and cyclic ether monomers such as ethylene oxide.

In some preferred embodiments, the present invention comprises coatings and medical devices having coatings comprising triblock copolymers having endblocks comprising a grafted copolymer wherein the grafts contain (a) one or more hydrophilic chains, including polymers of ethylene oxide (PEO), polymers of vinylpyrrolidone (PVP), poly(hydroxyacrylates), poly(hydroxymethacrylates), or a combination thereof, arranged in a repeating (e.g., alternating), random, statistical or gradient distributions. In other preferred embodiments, the grafts contain chains comprising one or more hydrophobic polymer chains such as polymers of methyl methacrylate (PMMA), or polystyrene, either singly or in combination, arranged in a repeating (e.g., alternating), random, statistical or gradient distribution. The grafts can employ a combination of both hydrophilic and hydrophobic monomers that exhibit desired drug diffusion and release properties. The hydrophilic and/or hydrophobic monomers can be selected from any one or more monomer species, including but not limited to those numerous examples specifically listed above for preparation of low and other polymer blocks and endblocks.

In certain embodiments, the drug release rate is controlled by blending hydrophobic or hydrophilic polymers with the graft copolymers described herein. In one exemplary embodiment, the invention provides a blend comprising a triblock graft copolymer blended with a polystyrene-polyisobutylene-polystyrene (SIBS) triblock copolymer. The triblock graft copolymer, in a preferred embodiment, comprises a midblock of polysiloxane and end blocks of poly(methyl methacrylate)-graft-polystyrene copolymer.

As will be appreciated by one of skill in the art, the copolymers of the present invention may be synthesized according to known methods, including ionic and, in particular, radical polymerization methods such as azobis(isobutyronitrile)- or peroxide-initiated processes, and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes. These methods are well-detailed in the literature and are described, for example, in an article by Pyun and Matyjaszewski, *Synthesis of Nanocomposite Organic/Inorganic Hybrid Materials Using Controlled/"Living" Radical Polymerization*, Chem. Mater., 13:3436-3448 (2001), the contents of which are incorporated by reference in its entirety.

In polymerizations of a monomer (M, in scheme below) via ATRP, radicals are generated by the redox reaction of organic halides such as alkyl halides (RX, in scheme below) with transition-metal complexes (Met$_{+n}$, in scheme below). Initiators typically used are α-haloesters (e.g., ethyl 2-boroisobutyrate and methyl 2-bromopropionate) or benzyl halides (e.g., 1-phenylethyl bromide and benzyl bromide). A wide range of transition-metal complexes, such as Ru- (e.g., Grubbs catalyst), Cu-, and Fe-based systems are employed. For Cu-based systems, ligands such as 2,2'-bipyridine and aliphatic amines are typically employed to control both the solubility and activity of various ATRP catalysts. A typical ATRP mechanism is illustrated by the following scheme:

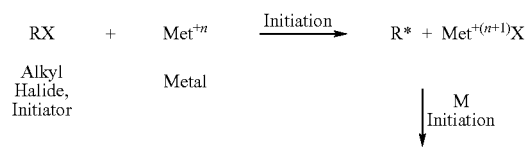

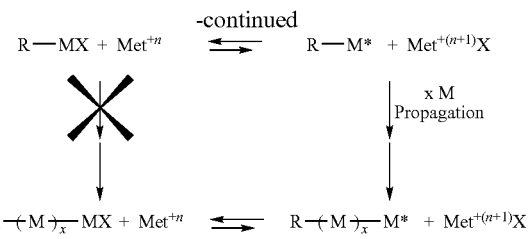

The copolymers of the medical devices of the present invention can be synthesized, for example, by a free radical process that comprises: (a) providing a macro-initiator, wherein said macro-initiator is terminated with one or more functional groups capable of initiating polymerization by living free-radical polymerization and (b) conducting a living free radical polymerization reaction in the presence of (i) a macro-monomer comprising said side chain and further comprising a free radical polymerizable end group, and (ii) a free-radical polymerizable comonomer, or a combination of comonomers, each containing a polymerizable unsaturated group. Preferably, the end group is terminally unsaturated and the polymerizable comonomer is an unsaturated monomer.

The polymers of the present invention can also be synthesized using a di-functional free radical initiator such as dimethyl-2,6-heptanedioate, which is used to polymerize, for example, acrylate monomers (e.g., ethyl acrylate) to form a polyacrylate macro-initiator.

A "macro-monomer" as used herein is a macromolecule, commonly a polymer, which has one reactive group, often as an end-group, which enables it to act as a monomer molecule, contributing only a single monomeric unit to a chain of the final macromolecule. Each macro-monomer molecule is attached to the main chain of the final polymer by reaction of only one monomeric unit in the macro-monomer molecule. Homopolymerization or copolymerization of a macro-monomer yields comb or graft polymers. For example, a long-chain vinyl polymer or oligomer (as used herein, an oligomer is a polymer containing from 2-9 constitutional units) that has a polymerizable double bond at the end of the chain is a macro-monomer.

Examples of some commonly employed free radical initiator compounds include hydroperoxide, peroxides, such as diacetyl peroxide, di-tert-butyl peroxide, di-benzoyl peroxide, and azo compounds, such as azobis(isobutyronitrile), tertiary butyl perbenzoate, di-cumyl peroxide and potassium persulfate.

Examples of macro-initiators include polysiloxanes, polyisobutylene, other polyolefins, or polyacrylates, all having one or more functional groups capable of initiating a subsequent polymerization by living free-radical polymerization techniques. In some embodiments, the macro-initiator is a mono- or di-functional polydimethylsiloxane (PDMS) containing benzyl halide (e.g., benzyl chloride) or 2-bromoisobutyrate end groups. Generally, PDMS with either vinyl or silane (Si—H) end groups are reacted with various alkenes via hydrosilylation to introduce functionality to the PDMS chain ends. In one preferred embodiment, the macro-initiator comprises a monofunctional 2-bromoisobutyrate-terminal PDMS.

Examples of macro-monomers include polystyrene, polyethylene oxide, polyvinylpyrrolidone, polymethylmethacrylate, each with a polymerizable end group, for example, a group that provides terminal unsaturation, such as alkyl methacrylate-terminated polystyrene.

Examples of comonomers include unsaturated monomers or a combination of monomers, each containing a polymerizable unsaturated group, such as alkyl methacrylates, alkyl acrylates, hydroxyalkyl methacrylates, vinyl esters or styrene.

Medical devices for use in conjunction with the present invention include essentially any medical device for which controlled release of a therapeutic agent is desired. Examples of medical devices include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, and any coated substrate (which can comprise, for example, glass, metal, polymer, ceramic and combinations thereof) that is implanted or inserted into the body and from which a therapeutic agent is released. Examples of medical devices further include patches for delivery of therapeutic agent to intact skin and broken skin (including wounds); sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and tissue engineering scaffolds for cartilage, bone, skin and other in vivo tissue regeneration.

The medical devices of the present invention include medical devices that are used for either systemic treatment or for the localized treatment of any mammalian tissue or organ. As used herein, "treatment" refers to the prevention of a disease or condition, the reduction or elimination of symptoms associated with a disease or condition, or the substantial or complete elimination of a disease or condition. Preferred subjects are mammalian subjects and more preferably human subjects. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, vagina, uterus, ovary, and prostate; skeletal muscle; smooth muscle; breast; dermal tissue; cartilage; and bone.

Specific examples of medical devices for use in conjunction with the present invention include vascular stents, which deliver therapeutic agent into the vasculature for the treatment of restenosis. In these embodiments, the release region is typically provided over all or a portion of a stent substrate, and is typically in the form of one or more carrier layers (in which case therapeutic agent is disposed within the release layer) or one or more barrier layers (in which case the release layer is disposed over a therapeutic-agent containing region).

"Therapeutic agents," "pharmaceutically active agents," "pharmaceutically active materials," "drugs," and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; and (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomycin D, Resten-NG, Ap-17, abciximab, clopidogrel and Ridogrel, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Therapeutic agents also include ablation agents, sufficient amounts of which will result in necrosis (death) of undesirable tissue, such as malignant tissue, prostatic tissue, and so forth. Examples include osmotic-stress-generating agents, for example, salts such as sodium chloride or potassium chloride; organic solvents, particularly those such as ethanol, which are toxic in high concentrations, while being well tolerated at lower concentrations; free-radical generating agents, for example, hydrogen peroxide, potassium peroxide or other agents that can form free radicals in tissue; basic agents such as sodium hydroxide; acidic agents such as acetic acid and formic acid; enzymes such as collagenase, hyaluronidase, pronase, and papain; oxidizing agents, such as sodium hypochlorite, hydrogen peroxide or potassium peroxide; tissue fixing agents, such as formaldehyde, acetaldehyde or glutaraldehyde; and naturally occurring coagulants, such as gengpin.

A wide range of therapeutic agent loadings can be used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the release region(s), the nature of the medical device, and so forth.

EXAMPLE

Synthesis of Poly(dimethylsiloxane) Block Copolymer with Poly(methyl methacrylate)-graft-polystyrene Copolymer Endblock(s)

Copolymers in accordance with the present invention, e.g., copolymers comprising a low $T_g$ block and a graft copolymer endblock, are prepared by the living free radical co-polymerization of a polymer with terminal unsaturation (macromonomer) and a comonomer having an unsaturated functional group. Specifically, di-block and tri-block copolymers from PDMS macroinitiators are produced from the polymerizations of acrylates and methacrylates from mono- and di-functional PDMS containing benzyl chloride or 2-bromoisobutyrate end groups.

Mono- and di-hydride-terminated PDMS as well as other telechelic PDMS compounds with different kinds of end groups are readily prepared by condensation polymerizations and are commercially available. A silicone macro-initiator is prepared by the hydrosilylation of hydrosilyl-terminated polydimethylsiloxane (Gelest) (Mn=4500-33,900; Mw/Mn=1.2-2.4) with vinyl benzyl chloride, as described previously in Y. Nakagawa et al., *Polymer*, 1998; 39(21): 5163-5170, the contents of which are hereby incorporated by reference in their entirety. Specifically, a di-functional PDMS (Mw=9800; Mw/Mn=2.4) possessing vinyl end groups is reacted with [2-[4-(chloromethyl)phenyl]ethyl]-dimethylsilane to yield a benzyl chloride functional PDMS.

Alternatively, hydrosilylation of hydrosilyl-terminated PDMS under air is conducted with allyl-2-bromoisobutyrate or 3-butenyl-2-bromoisobutyrate using tetrahydrofuran as the solvent, as described in P. Miller and J. Matyjaszewski, *Macromolecules*, 1999; 32(26):8760-8767, the contents of which are hereby incorporated by reference in their entirety, to form mono- and di-functional PDMS having 2-bromoisobutyrate end groups.

Since 2-bromoisobutyrates are efficient initiators for the polymerizations of styrene, acrylates, and methacrylates, a macro-initiator containing this functional group is used in living free-radical polymerization techniques. Allyl-2-bromoisobutyrate is synthesized by the esterification of allyl alcohol with 2-bromoisobutyryl bromide in a tetrahydrofuran/triethylamine solution. This compound is used in hydrosilylations with di-functional hydrosilyl-terminated PDMS in the presence of Karstedt's catalyst in tetrahydrofuran at reflux. These macroinitiators can be used to polymerize a variety of monomers by ATRP. Different molecular weight macro-initiators may also be used to vary the synthesis of these copolymers.

For example, a copolymer with a PDMS mid-block and end-blocks consisting of a poly(methylmethacrylate) main chain with poly(styrene) side chains can be produced by the following method. A di-functional 2-bromoisobutyrate-terminated PDMS is used to initiate the co-polymerization of methylmethacrylate monomer with a methacrylate-terminated polystyrene. The di-functional 2-bromoisobutyrate-terminated PDMS is placed in a flask with copper chloride (CuCl) and toluene. The methyl methacrylate and the methacrylate-terminated polystyrene are also charged into the flask. The solution is placed under an inert atmosphere by purging the system with nitrogen. A homogeneous catalyst $(dnNbpy)_2$ is added to the system after the nitrogen purge. Oxygen is removed from the solution by sparging with nitrogen. The polymerization is run at 90° C.

Synthesis of Polyolefin Block Copolymer with Poly(methyl methacrylate)-graft-polystyrene Copolymer Endblock(s)

As will be readily appreciated by one of skill in the art, copolymers formulated where the endblocks are graft copolymers comprising a low $T_g$ main chain can be formed using a di-functional-terminated polyolefin. For example, a polyolefin copolymer can be prepared by reacting a di-hydroxy-terminated poly(olefin) with 2-bromo-isobutyryl bromide. This forms a macroinitiator with two α-bromoester groups. These α-bromoester groups can be used to initiate the co-polymerization of methyl methylacrylate monomer with a methacrylate-terminated polystyrene. The poly(methyl methacrylate) comprises the main chain of the end block, and the methacrylate-terminated polystyrene forms the side chains of the endblocks. This polymerization occurs via atom transfer radical polymerization techniques or other controlled/living radical polymerization methods.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A medical device comprising: (a) a release region and (b) a therapeutic agent disposed within or beneath said release region, said release region comprising a copolymer that comprises (i) a low $T_g$ block displaying a glass transition temperature ($T_g$) that is below 25° C., said low $T_g$ block selected from a polyacrylate block, a polymethacrylate block, a polyester block, a polyalkene block, a poly(halogenated alkene) block, and a poly(siloxane) block; and (ii) a plurality of graft copolymer endblocks, said graft copolymer endblocks comprising (a) a polymethylmethacrylate main chain and (b) a plurality of side chains selected from polyethylene oxide, polyvinylpyrrolidone, polymethylmethacrylate, and polystyrene.

2. The device of claim 1, wherein said copolymer is made by a process that comprises (a) providing a macro-initiator that is terminated with one or more functional groups capable of initiating polymerization by living free-radical polymerization and (b) conducting a living free radical polymerization reaction in the presence of (i) a macro-monomer comprising said side chain and further comprising a free radical polymerizable end group, and (ii) a free-radical polymerizable comonomer.

3. The device of claim 2, wherein said free radical polymerizable end group is terminally unsaturated and wherein the polymerizable comonomer is an unsaturated monomer.

4. The device of claim 2, wherein the macro-monomer is selected from polystyrene, polyethylene oxide, polyvinylpyrrolidone, polymethylmethacrylate, each having a free radical polymerizable end group.

5. The device of claim 2, wherein the comonomer is methylmethacrylate.

6. The device of claim 2, wherein the macro-initiator is selected from a polysiloxane, a polyacrylate, or a polyalkene, each having a free radical polymerizable end group.

7. The device of claim 2, wherein the macro-initiator is selected from polydimethylsiloxane having a free radical polymerizable end group and polyisobutylene having a free radical polymerizable end group.

8. The device of claim 1, wherein the release region further comprises a supplemental polymer comprising polystyrene-poly(ethylene/butylene)-polystyrene, polystyrene-polyisobutylene-polystyrene, or styrene maleic anhydride copolymer.

9. The device of claim 1, wherein said low $T_g$ block is a biostable polymer block.

10. The device of claim 1, wherein said low $T_g$ block comprises a polyalkene block.

11. The device of claim 10, wherein said polyalkene block is a polyisobutylene block.

12. The device of claim 1, wherein said low $T_g$ block comprises a polyisobutylene block or a polysiloxane block.

13. The device of claim 1, wherein said copolymer is selected from the group consisting of a triblock copolymer and a star copolymer.

14. The device of claim 1, wherein said release region is a carrier region that comprises said therapeutic agent.

15. The device of claim 1, wherein said release region is a barrier region disposed over a therapeutic-agent-containing region that comprises said therapeutic agent.

16. The device of claim 1, wherein said release region is in the form of a coating layer that covers all or a part of said medical device.

17. The device of claim 1, wherein said medical device is an implantable or insertable medical device.

18. The device of claim 17, wherein said implantable or insertable medical device is selected from a catheter, a guide wire, a balloon, a filter, a stent, a stent graft, a vascular graft, a vascular patch and a shunt.

19. The device of claim 17, wherein said implantable or insertable medical device is adapted for implantation or insertion into the coronary vasculature, peripheral vascular system, esophagus, trachea, colon, biliary tract, urinary tract, prostate or brain.

20. The device of claim 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

21. The device of claim 1, wherein said low $T_g$ block is selected from a polyacrylate block, a polyalkene block, and a poly(siloxane) block.

22. The device of claim 1, wherein said low $T_g$ block is selected from a polybutylacrylate block, a polyisobutylene block, and a polydimethylsiloxane block.

23. The device of claim 1, wherein said plurality of side chains are polystyrene chains.

24. The device of claim 4, wherein the macro-initiator is selected from a polysiloxane, a polyacrylate and a polyalkene, each having a free radical polymerizable end group.

25. The device of claim 24, wherein the comonomer is methylmethacrylate.

26. A method of forming the medical device of claim 1, comprising: (a) providing a solution comprising (i) a solvent system and (ii) said copolymer; and (b) forming said release region from said solution by removing said solvent system from said solution.

27. The method of claim 26, wherein said solution further comprises a therapeutic agent in dissolved or dispersed form.

28. The method of claim 26, wherein said solution is applied over a therapeutic-agent-containing region that comprises said therapeutic agent.

29. The method of claim 26, wherein said release region is formed by a technique comprising a spraying process.

30. A medical device comprising: (a) a release region and (b) a therapeutic agent disposed within or beneath said release region, said release region comprising a copolymer that comprises (i) a low $T_g$ block displaying a glass transition temperature ($T_g$) that is below 25° C., said low $T_g$ block comprising one or more hydrophobic polymer chains; and (ii) a graft copolymer endblock, said graft copolymer endblock comprising a main chain and a plurality of side chains, which do not comprise a polysiloxane, wherein said low $T_g$ block is a polydimethylsiloxane block, wherein said main chain is a polymethylmethacrylate chain and wherein said side chains are polystyrene chains.

31. A medical device comprising: (a) a release region and (b) a therapeutic agent disposed within or beneath said release region, said release region comprising a copolymer that comprises (i) a low $T_g$ block displaying a glass transition temperature ($T_g$) that is below 25° C., said low $T_g$ block selected from a polyacrylate block, a polymethacrylate block, a polyester block, a polyalkene block, a poly(halogenated alkene) block, and a poly(siloxane) block; and (ii) a plurality of graft copolymer endblocks, said graft copolymer endblocks comprising (a) a poly(alkyl methacrylate) main chain and (b) a plurality of polystyrene side chains,
    wherein said copolymer is made by a process that comprises (a) providing a macro-initiator that is terminated with one or more functional groups capable of initiating polymerization by living free-radical polymerization and (b) conducting a living free radical polymerization reaction in the presence of (i) a macro-monomer comprising alkyl methacrylate-terminated polystyrene, and (ii) a free-radical polymerizable comonomer.

* * * * *